(12) United States Patent
Carano et al.

(10) Patent No.: US 6,220,856 B1
(45) Date of Patent: *Apr. 24, 2001

(54) DEVICE FOR ORTHOPEDIC AND/OR ORTHODONTIC TREATMENT

(75) Inventors: Aldo Carano, Taranto; Mauro Testa, Avigliana, both of (IT)

(73) Assignee: Micerium S.R.L., Avegno (IT)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/172,993

(22) Filed: Oct. 14, 1998

(30) Foreign Application Priority Data

Oct. 15, 1997 (IT) .............................. SV97U0008

(51) Int. Cl.⁷ ...................................... A61C 3/00
(52) U.S. Cl. .................................................. 433/7
(58) Field of Search .................. 433/7, 18, 19, 433/21, 22, 23

(56) References Cited

U.S. PATENT DOCUMENTS

| 3,293,747 | 12/1966 | Denholtz | 433/21 |
| 4,202,100 | 5/1980 | Foster | 433/7 |
| 4,571,178 | 2/1986 | Rosenberg | 433/18 |
| 4,723,910 | 2/1988 | Keller | 433/7 |
| 5,022,855 | 6/1991 | Jeckel | 433/18 |
| 5,064,370 | 11/1991 | Jones | 433/21 |
| 5,564,920 | * 10/1996 | Klapper et al. | 433/7 |
| 5,645,422 | 7/1997 | Williams | 433/7 |
| 5,769,631 | 6/1998 | Williams | 433/7 |
| 5,785,520 | 7/1998 | Carano et al. | 433/7 |

OTHER PUBLICATIONS

"Modifications of the Distal Jet" by S. Jay Bowman, DMD, MSD, Journal of Clinical Orthodontics vol. XXXII No. 9 Sep. 1998.

* cited by examiner

Primary Examiner—John J. Wilson
(74) Attorney, Agent, or Firm—Foley & Lardner

(57) ABSTRACT

A device for the orthodontic and/or orthopedic correction in a dental arch. The device includes at least one thrust or traction element attached to a first set of teeth at one end a second set of teeth at an opposite end. The thrust or traction element includes a pair of telescopically engaged elongated members, a pair of stops, and a spring. At least one of the stops can be adjusted in an axial direction of the elongated members to regulate the amount of compression in the spring. The thrust or traction forces are exerted at a level of the basal gingiva and attached to the teeth of the first and second sets as close to the cervical zone as possible. The device permits expansion and contraction of the dental arch in a direction perpendicular to the longitudinal axis of the arch, as well as lengthening and shortening of the dental arch in the longitudinal direction. All the forces generated the by thrust or traction elements are preferably absorbed by and transferred among the teeth in the first and second sets.

24 Claims, 3 Drawing Sheets

DEVICE FOR ORTHOPEDIC AND/OR ORTHODONTIC TREATMENT

TECHNICAL FIELD

The invention has as its object a device for orthodontic or orthopedic correction of the maxilla and its dental units, as well as for orthodontic correction of the dental units in the mandible.

BACKGROUND OF THE INVENTION

Devices for orthodontic and orthopedic expansion or contraction of the maxilla are known. Such known devices may comprise means for anchoring the device to two or more molars positioned on opposite maxillary half-arches divided by the median antero-posterior axis. The devices further comprise thrust or traction agents affixed to the anchoring means and acting in a direction substantially perpendicular to the antero-posterior axis, i.e., in the direction of distancing the two anchoring molars from each other or of moving them closer together.

At present there are two known types of these devices. In a first known type, the thrust or traction agents are of the wrench or screw type. More particularly, a structure composed of conjunction and of stiffening elements connects the anchoring means of each of the two opposed molars to two terminals which each present at least one threaded opening coaxial respective to each other, with the threads running in opposite directions. A pin having two threaded ends, with the threads running in opposite directions, is engaged in the corresponding threaded openings of the two terminals. A middle portion of pin includes means for actuating the pin in rotation, such as with the use of suitable instruments. By rotating the threaded pin, it is therefore possible to move the two terminals farther away or closer together, to thereby control the expansion or contraction action of the maxilla.

Despite that the above-described types of devices make it possible to exert forces of expansion or contraction perfectly oriented in a direction perpendicular to the antero-posterior median of the maxilla (i.e., parallel to the direction of expansion or contraction desired), an appreciable disadvantage of these devices is that the expansion or contraction action is of very short duration once the "loading" action (i.e., the twisting of the pin) is terminated. The short duration is the result of the loading structure being essentially rigid. Moreover, these devices do not allow an expansion or contraction action of a desired amount to be exerted in a progressive manner. Rather, the traction or expansion force is exerted on the teeth in an almost "traumatic" manner (i.e., all at once or over an extremely limited length of time).

The application of these devices therefore is especially painful for the patient. Furthermore, this mode of operation of the device means that the medical personnel must execute frequent adjustments and trials with the thrust or traction means in order progressively to achieve, in small increments, the desired effect of expansion or contraction of the maxilla.

A second known type of device makes it possible to overcome the drawbacks of this first known type that relate to the rigid structure of the thrust and traction means. More specifically, in the second type of known device the thrust and traction means are made up of elastic elements that, in the application phase, are pre-loaded to a pre-set level. Presently, the elastic means are made up, however, of a metal wire that presents a certain elasticity and that is bent in such manner that it exerts an expansion or contraction force. To exert the force in the expansion direction, for example, the elastic metal wire may be bent in such manner as to form a handle with its terminal portions spread apart. While to exert a force of traction, the metal wire may be bent in such manner as to form, for example, a spiral with end parts that intersect each other.

These elastic means exert a progressive action of expansion and compression that, however, because of their structure, is of very short duration, requiring frequent interventions for additional loading of force by means of further deformations. This type of device presents an additional drawback of causing the support teeth to unacceptably tip from the desired vertical orientation and to cause an undesirable V-shaped gap in the arch form (anterior vestibulation).

It is therefore an object of the present invention to create an orthodontic and orthopedic device in such a manner that it does not suffer from the above-described drawbacks of the presently known devices. It is also an object of present invention to provide a low cost device that is simple to install and adjust.

SUMMARY OF THE INVENTION

The invention achieves the above ends with a device for making orthodontic or orthopedic corrections in a dental arch. The device includes thrust or traction means comprising at least one pair of terminals and an elastic means. The terminals of each pair are connected to means for anchoring them to at least one tooth on opposite sides of the dental arch or, alternatively, to two longitudinally spaced teeth on the same side of the dental arch. The two terminals of each pair telescopically engage each other in reciprocal sliding motion in a direction of expansion or contraction of the dental arch or, alternatively, in a direction of lengthening or shortening of the dental arch. The elastic means are positioned intermediate the two terminals of each pair and rest against stop elements which are adjustable to regulate a desired amount of thrust or traction force generated by the elastic means.

According to an improvement the terminals of each pair are constituted by a tubular element and an rod element sliding inside the tubular element.

According to a further improvement, each one of the two terminals carries at least one stop element, and the elastic means comprises a helix-shaped spring positioned between the two locating elements or radial enlargements. At least one of the stop elements can slide along the associated terminal and be locked into a desired position for setting the amount of force.

In a preferred form of execution, one of the stop elements comprises a small buckle that is slidable along the tubular terminal and which can be locked into position by tightening a radial screw or threaded pin screwed in a radial threaded perforation of the small buckle.

The terminals of the thrust or traction means may be either connected rigidly or elastically. For example, a rigid connection may be accomplished by soldering the thrust or traction means to the anchoring means or to a conjunction and stiffening structure affixed to the anchoring means, or an elastic connection may be accomplished by means of elastic ties that yield to pressure.

In order to guarantee that, as much as possible, the traction or expansion force is indeed exerted only in the desired direction (as is desirable to eliminate the effect of anterior vestibulation of the arch), it is possible to provide the anchoring on two teeth. That is, the device is anchored either on two molars, or two pre-molars (i.e., bicuspids), or on some combination thereof, with at least one tooth selected from each of the two dental half-arches. In this case, each pair of attachment points (e.g. wire hooks) symmetrically opposed with respect to the antero-posterior axis that defines the half-arch are connected together by means of a pushing device or with a traction means. The two pushing elements or the pair of traction means are oriented in parallel direction with respect to the direction in which they exert their thrust or contraction force.

The elements for attaching the pair of thrust elements or traction means onto the anchoring teeth either can be independent among themselves or they can form a type of framework. The framework can be a rigid connection because of the presence of the elastic means.

From the above, a number of the advantages of the present invention are made clear. First, the device according to the present invention provides an expansion or traction action or force which is progressive, thus overcoming the drawbacks of anterior vestibulation and of a slanting vestibule of the teeth. Moreover, the progressive nature of the force permits the maintaining and perfecting of the structural stability of the expansion or contraction action by means of a wrench, relative to the precise orientation of the direction in which these forces are exerted. Accordingly, not only will this efficiently avoid all of the expansion or contraction force components that might cause undesirable effects of displacement of the tooth or teeth, but such effects may be intentionally induced whenever necessary, as they are perfectly controllable and adjustable with the device of the present invention. Thus, for example, the expansion action may be combined with a rotation action of the teeth.

Moreover, with the preferred construction of the thrust or traction means, the progressive action is exerted for a longer period of time as compared to that of the known devices. In addition, the field of action of the thrust and traction means turns out to be larger than in the known devices. Therefore, fewer adjustments and re-activations are required. Even more, these interventions are more easily executed and the forces involved easily adjustable because of the use of the helix-shaped springs as elastic elements and the simple means of regulating the relative positions of the locating elements between which the springs work.

Furthermore, the preferred construction permits the reduction of the measurements or size necessary for the construction of the individual devices. That is, since the thrust or traction elements of the type provided herein have a field of action substantially more extended, they are thus adaptable to measurements that vary greatly among themselves.

The above improvements of the invention are the object of the dependent claims.

BRIEF DESCRIPTION OF THE DRAWINGS

The invention will be better understood from the following description of the exemplary embodiments and from the illustrations in the attached drawings, in which.

DETAILED DESCRIPTION OF PREFERRED EMBODIMENTS

Figure 1:
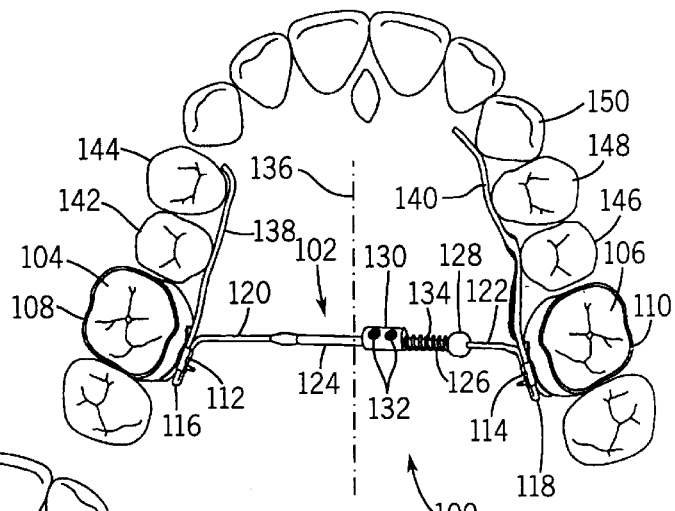
FIG. 1 shows an occlusal view of the maxillary arch with a device according to one embodiment of the invention elastically connected to opposed teeth of the arch and disposed for orthodontic expansion in a direction substantially perpendicular to a longitudinal direction of the arch.

With reference to FIG. 1, an orthodontic expansion device 100 having a single thrust element 102 is shown hooked to two molars 104, 106 of the upper maxillary by hooking bands of strips 108, 110. More particularly, strips 108, 110 include lingual tubes 112, 114, respectively, in which respective hooks 116, 118 of respective conjunction elements 120, 122, formed by a metal wire, are engaged in corresponding terminals 124, 126 of thrust element 102.

One terminal 124 of thrust element 102 includes a cylindrical tubular element while the other terminal 126 of thrust element 102 includes an unthreaded rod telescopically sliding in the tubular element of terminal 124. The tubular element of terminal 124 is preferably soldered to the end of the metallic conjunction element 120. The rod of terminal 126 preferably is a unitary metal wire which also forms conjunction element 122. Alternatively, the rod of terminal 126 could be a separate element soldered to the end of conjunction element 122. Terminal 126 includes a bead-shaped stop structure 128 which can be fixed at a desired axial location along the rod or conjunction wire by suitable means. Alternatively or in addition, the rod or conjunction wire itself of terminal 126 could be bent to include a radial shoulder (not shown), which radial shoulder would be connected to terminal 126 in transverse orientation therewith or even in a partially radial one. Terminal 126 formed by the tubular element has situated thereon a small buckle 130 provided with at least one radial passage that is threaded and run from the outside to the inside of buckle 130. Preferably, buckle 130 includes two such radial passages, each of which is configured for receiving a small threaded screw 132 therein, which can be used to lock buckle 130 into a fixed position about terminal 126. As an alternative, the inner diameter surface of the buckle could itself be threaded, and the outer surface of the tubular element provided with matching threads, in which case the buckle could then be threaded into place over the tubular element.

Situated intermediate stop structure 128 on the rod of terminal 124 and buckle 130 on the tubular element of terminal 126, there is inserted a helix-shaped spring 134 that can be compressed by suitably axially positioning buckle 130 along the tubular element. In this manner, spring 134 can be loaded in a direction of telescopic reciprocal sliding movement of terminals 124, 126.

The axis of the terminals 124 and 126 (i.e., the direction of telescopic reciprocal sliding motion of the terminals) is oriented parallel to the desired direction of expansion, which direction is substantially perpendicular to the longitudinal axis 136 of the arch. By appropriate shaping of the elements 120, 122, that join respective terminals 124, 126 to strips 108, 110, respectively, it is possible not only to expand the teeth to which strips 108, 110 are secured but also one or more additional teeth. For example, conjunction elements 120, 122 can be provided with extensions 138, 140 for ensuring that adjacent teeth 142, 144 (illustrated as the first and second bicuspids) along one side of the arch and teeth 146-150 (illustrated as the first and second bicuspids and one canine) along the other side of the arch are expanded as well. Moreover, by appropriate shaping of the metallic conjunction elements 120, 122 (e.g., by appropriate bending of hooks 116, 118), and/or by appropriate positioning of lingual tubes 112, 114, it is possible to combine the desired expansion force with an additional force for causing rotation of one or more of the teeth to which the tubes 112, 114 are secured.

It should also be noted that the thrust element 102 is positioned at a location and oriented so as to apply the thrust force along a line which passes through or close to the center of resistance of the teeth 104, 106. More particularly, the thrust element 102 extends at the lowest possible position within the basal zone of gingiva and is attach to teeth 104, 106 as close to the cervical zone as possible (best seen in FIG. 6), so that the thrust force passes as close as possible to the resistance points of the teeth. This arrangement largely suppresses those components of the force which act so as to tilt the teeth from their correct vertical orientations, i.e., it provides bodily or integral movement of the teeth without causing undesired tilting. The further details of positioning the thrust force (or the traction force described below) in the most preferred manner, as well as the advantages resulting therefrom, can be found in U.S. Pat. No. 5,785,520, issued Jul. 28, 1998, the entire contents of which is incorporated by reference herein.

Figure 2:
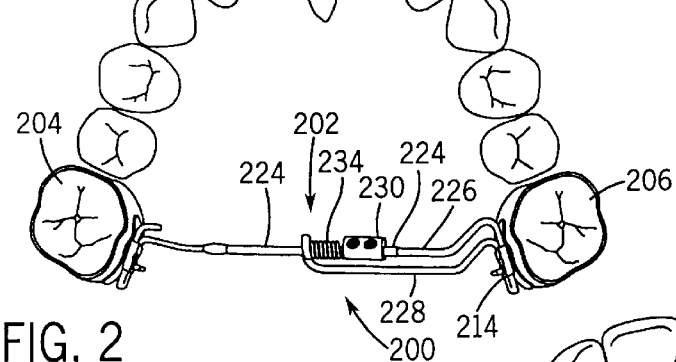
FIG. 2 shows and occlusal view of the maxillary arch with a device according to yet another embodiment of the invention elastically connected to opposed molar teeth of the arch and disposed for orthodontic constriction of the molar teeth in a direction substantially perpendicular to a longitudinal direction of the arch.

It is also possible by suitably configuring the various elements of the invention to provide a traction force rather than an expansion force. FIG. 2 shows one exemplary device 200 for obtaining this opposite force. For brevity and clarity, elements in FIG. 2 corresponding (i.e., providing the same or similar functions) to those in FIG. 1 will be referenced by the same numbers, but with the prefix "2" instead of the prefix "1". For such corresponding elements, generally no further description will be provided herein except with reference to the differences between the two embodiments.

At the outset, it can immediately be seen that helix spring 234 in traction element 202 is on the opposite side of small buckle 230 than was spring 134 in thrust element 102 (i.e., spring 234 is on the left of buckle 230 as illustrated in FIG. 2). In addition, rather than providing terminal 226 (i.e., the terminal including the rod element) with a bead-shaped stop structure 128(as in FIG. 1), terminal 226 is provided with an elongated hook element 228 which extends all the way from lingual tube 214 to the far side of buckle 230 where it loosely hooks around the tubular element of terminal 224. Thus, since spring 234 is positioned between buckle 230 and the sliding hook portion of element 228, it provides a pushing action which in this case forces the rod of terminal 226 further into telescopic sliding movement with the tubular element of terminal 224. That is, terminals 224 and 226 are telescoped towards each other, thus contracting the teeth 204, 206 toward the median-posterior axis. In this embodiment, it can be seen that the desired traction force is regulated primarily by adjustment of the axial position of buckle 230 along tubular element 224.

Figure 3:
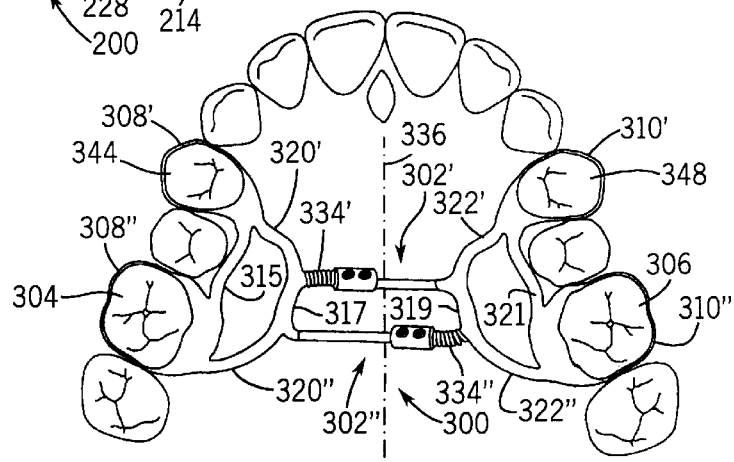
FIG. 3 shows an occlusal view of the maxillary arch with a device according to another embodiment of the invention rigidly connected to opposed teeth of the arch and disposed for orthopedic expansion in a direction substantially perpendicular to a longitudinal direction of the arch.

Turning now to FIG. 3, a device 300 having a pair of thrust elements 302', 302" is shown hooked to teeth on opposite sides of the upper maxillary in an arrangement for providing orthopedic expansion. In FIG. 3, elements similar to those in the above described embodiments of FIGS. 1 and 2 will be referenced by the same numbers, but preceded by the prefix "3" and optionally primed.

FIG. 3 shows thrust elements 302', 302" hooked to teeth 304, 344 by means of respective conjunction elements 320', 320" extending to bands or strips 308', 308" on one side of the half-arch, and hooked to teeth 306, 348 by means of respective conjunction elements 322', 322" for each band or strip 310', 310" on the other side of the half arch. The two thrust elements 302', 302" are oriented parallel with each other and spaced apart along the longitudinal axis 336 of the arch. The attachment ends of thrust elements 302', 302", as well as conjunction elements 320', 320" and 322', 322", are all connected among themselves by corresponding transverse elements 315, 317, 319, 321, which along with the conjunction elements form a rigid framework. It can be seen that the connecting elements 317 and 319 form stop structures for respective springs 334', 334", and thus no separate bead-shaped stops are required for springs 334', 334" to function.

It will of course be understood that instead of the rigid framework, the attachment of device 300 to the maxillary arch could be by means of elastic ties such as for example wire hooks formed on conjunction elements 320', 320", 322', 322" and lingual tubes provided on strips 308', 308", 310', 310", as shown in the embodiments of FIGS. 1 and 2.

With this configuration (i.e., the two thrust elements 302', 302" being oriented perpendicular to the longitudinal axis 336 of the arch and spaced apart from each other along longitudinal axis 336, and also being attached to multiple teeth on each side of the dental arch), there is ensured an expansion of the arch perfectly oriented in the desired direction. This avoids the effects of anterior vestibulation of the maxillary arch, that is, of an anterior opening of the arch.

From the foregoing embodiments, it should be clear that with slight modifications to the various elements a structure could be obtained to contract the maxillary arch instead of expand it. In particular, hook elements 328 (not shown) could be provided, while spring 234', 234" would be moved to the opposite sides of buckles 230', 230", i.e., similar to the embodiment illustrated and described above according to FIG. 2.

Figure 4:
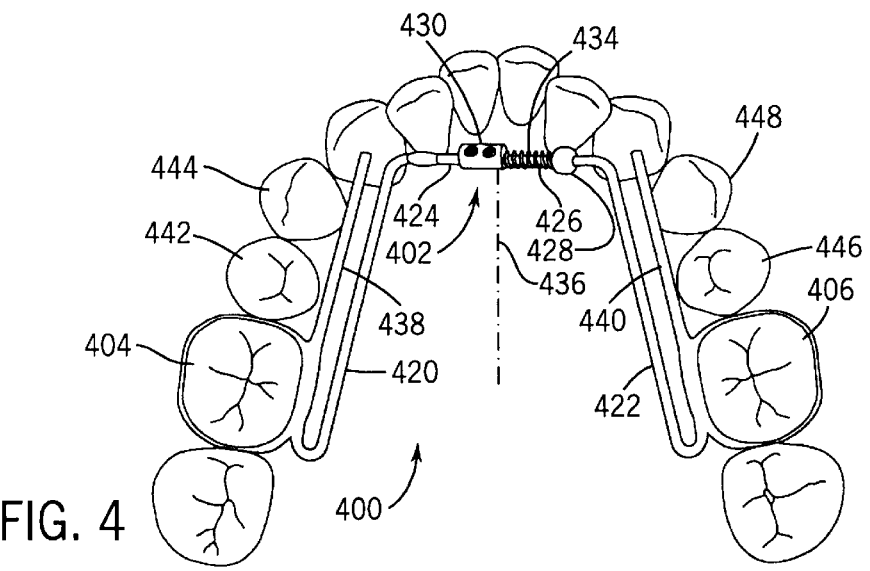
FIG. 4 shows an occlusal view of the mandibular arch with a device according to a further embodiment of the invention rigidly connected to the teeth and disposed for orthodontic expansion in a direction substantially perpendicular to a longitudinal direction of the arch.

Moreover, it is also possible by suitably configuring the various elements of the invention to provide a force for contracting or expanding teeth across the antero-posterior axis of the mandibular arch. For example, FIG. 4 illustrates one such embodiment, in particular, a device 400 for expanding the distance between two or more opposed teeth in the mandibular arch. Again, like elements share like reference numerals except for the prefix "4".

In FIG. 4, it can be seen that conjunction elements 420, 422 extend all the way or nearly all the way to the lingual sides of the anterior teeth, at which position a single thrust element 402 is positioned. This arrangement is designed to provide room for the tongue. Once again, the thrust element 402 is positioned in an orientation such that the telescopic reciprocal sliding movement of tubular element 424 and rod element 426 is in a direction substantially perpendicular to the longitudinal axis 436 of the mandibular arch. Similar to the first embodiment, a bead-shaped stop structure 428 is provided on the rod of terminal 426 to provide a stop in an opposed relationship with buckle 430 in order for spring 434 to push against. In addition, similar to with the third embodiment, although conjunction elements 420, 422 are secured to molars 404, 406 by a rigid connection, an elastic connection could be used instead. Also, similar to with the first embodiment, conjunction elements 420, 422 can be provided with extensions 438, 440 for ensuring that adjacent teeth 442, 444 along one side of the arch and teeth 446, 448 along the other side of the arch are expanded as well.

Figure 5:
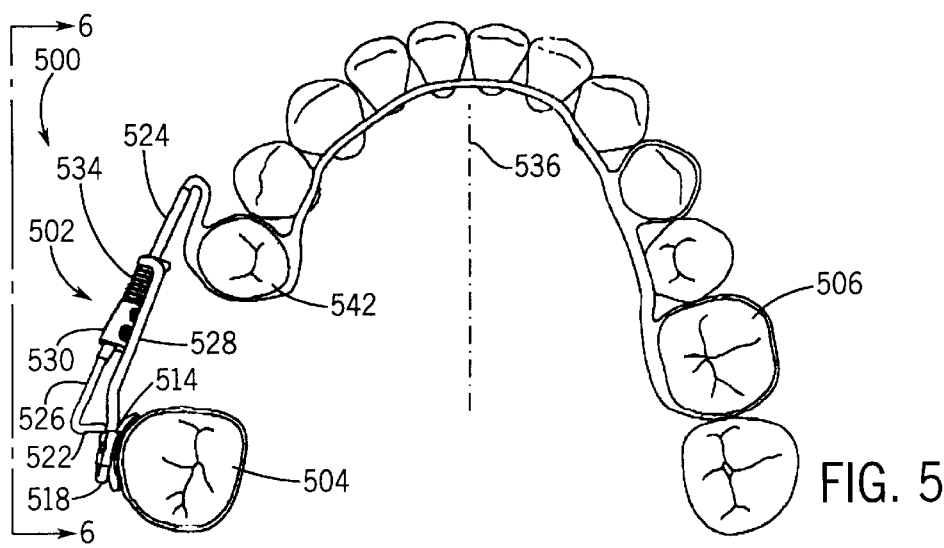
FIG. 5 shows an occlusal view of the mandibular arch with a device according to another embodiment of the invention elastically connected to the teeth and disposed for orthodontic constriction in a direction substantially parallel to a longitudinal direction of the arch.
Figure 6:
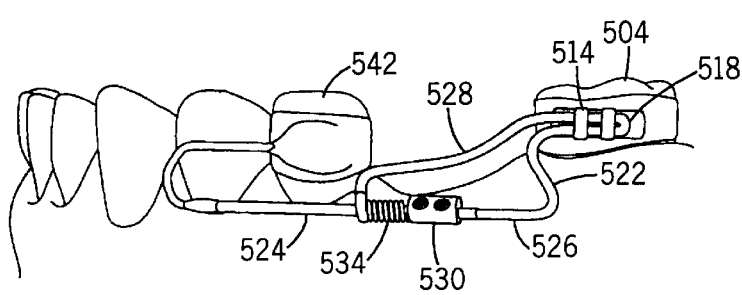
FIG. 6 shows a lateral view of the embodiment of FIG. 5 taken along the line 6—6 in FIG. 5.
Figure 7:
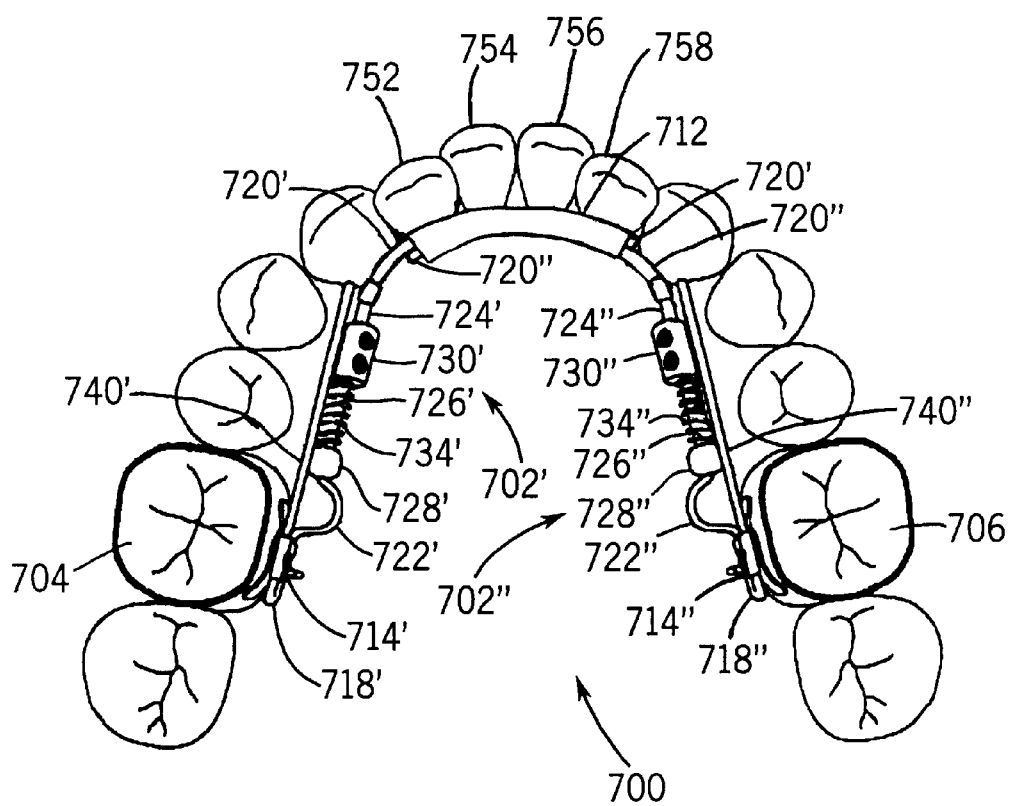
FIG. 7 shows an occlusal view of the mandibular arch with a device according to another embodiment of the invention elastically connected to the teeth and disposed for orthodontic expansion in a direction substantially parallel to a longitudinal direction of the arch.

It is also possible by suitably configuring the various elements of the invention to provide a force for lengthening or shortening a dental arch (i.e., orthodontic correction along the longitudinal axis of the maxillary or mandibular arch). For example, FIGS. 5 and 6 illustrate a device 500 for shortening the longitudinal distance between selected teeth in one half-arch of the mandibular arch, and FIG. 7 illustrates a device 700 for lengthening the longitudinal distance between selected teeth in both half-arches of the mandibular arch. Again, elements like those in the previously described embodiments will be denoted by like reference numerals but with the prefix "5" in FIGS. 5 and 6 and with the prefix "7" in FIG. 7.

In FIGS. 5 and 6, it can be seen that the single traction element 502 is located on the buccal side of the teeth rather than the lingual side, as in the above-described embodiments. More specifically, traction element 502 includes a rod element 526, which is formed unitary with conjunction element 522 (i.e., they are both part of a single bent wire), and which includes a hook portion 518 elastically attached to lingual tube 514. The single wire forming rod element 526, conjunction element 522, and hook 518, also includes a forwardly extending hook element 528 which projects in front of buckle 530 to loosely wrap around rod element 524. Spring element 534 is located intermediate the forward end of hook element 528 and buckle 530, and thus provides a pushing force which draws molar 504 toward the front teeth in a direction substantially along the longitudinal axis 536 of the mandibular arch.

In FIG. 6, it can be clearly seen that the thrust element 502 extends at the lowest possible position within the basal zone of gingiva and is attach to teeth 504, 542 as close to the cervical zone as possible. As mentioned above, this arrangement positions the traction force so that it passes as close as possible to the resistance points of the teeth. If desired, a lingual wire 551 (see FIG. 5) can be provided to ensure that only the desired tooth correction is made. As illustrated, lingual wire 551 extends all the way around the mandibular arch and is rigidly connected to a corresponding molar 506 opposite from traction element 502.

Referring now to FIG. 7, the device 700 for expanding the mandibular arch is illustrated with a pair of thrust element 702', 702" located on the lingual sides of the bicuspid teeth of the two half-arches. Device 700 includes conjunction element 722', 722" which are appropriately bent so that respective hooked ends 718', 718" thereof can be connected to lingual tubes 714', 714" (attached to teeth 704, 706 as close to the cervical zone as possible), while also permitting thrust elements 702', 702" to extend at (and exert thrust forces along) the lowest possible position within the basal zone of gingiva. Preferably, rod element 726', conjunction element 722', hooked end 718', and an extension 740', are all formed from a single metal wire. As noted above, extension 740' can be appropriately bent laterally outward to apply an expansion force on selected teeth. Similarly, rod element 726", conjunction element 722", hooked end 718", and an extension 740", are preferably all formed from a single metal wire.

As with the foregoing embodiments, thrust elements 702', 702" include respective tubular elements 724', 724" (telescopically engaged with respective rod elements 726', 726"), small buckles 730', 730" (locked in place around the respective tubular elements 724', 724"), and springs 734', 734". Tubular elements 724', 724" are soldered to respective conjunction elements 720', 720". Conjunction elements 720', 720" include terminal portions which overlap each other along the lingual sides of the anterior incisors and are soldered together to form a unitary body 712 which presses against the lingual sides of the anterior incisors as close to the cervical zone as possible.

With the above-described arrangement, it can be seen that device 700 will have the effect of lengthening the mandibular arch (i.e., increasing the longitudinal spacing between molar 704 and the anterior teeth 752–758, and increasing the longitudinal spacing between molar 704 and the anterior teeth 752–758). This is accomplished, as in the foregoing devices, by using the force vectors generated by the thrust or traction elements to pit a first set of one or more teeth against a second set of one or more teeth. That is, by positioning the thrust and traction elements between the first and second sets of teeth such the forces are exerted along a low level of the basil gingiva, and by attaching the thrust elements to the teeth of the first and second sets as close as possible to the cervical zones, it is possible to move the tooth or teeth of either or both sets in a bodily manner, i.e., without any undesired tilting.

Moreover, with the present invention it is also possible not only to precisely determine the direction of the force vectors (i.e., along the direction of telescopic reciprocal movement of the rod and tubular elements), but also to calculate the exact amount of force being transferred to the teeth. That is, because pre-calibrated springs are used, it is possible to determine exactly the force being exerted by the spring by measuring how much it is compressed by the locking device. Such pre-calibration of the springs can be accomplished by simple technical tests. For example, it can easily be determined by testing that compressing a particular spring seven millimeters generates 180 grams of force deflection, and that compressing the same spring six millimeters generates 150 grams of force. With this arrangement, it is therefore possible to generate any amount of force desired.

It will be understood that the invention is not limited to the forms of execution described and illustrated, but it may be modified in construction, especially comprising the models that provide the same use. Rather, the invention is to be limited only by the scope of the claims attached hereto.

We claim:

1. A device for orthodontic or orthopedic correction in a dental arch, the device comprising:
    a pair of force generating elements oriented in parallel with each other and spaced apart along a longitudinal axis of the arch, each of the force generating elements having first and second opposite ends and including a pair of telescopically engaged elongated members, a pair of stops, and a spring coaxial with the members and positioned intermediate the stops, wherein at least one of the stops of each force generating element is adjustable along an axial direction of the elongated members to regulate an amount of spring compression; and
    a pair of rigid frameworks configured for attaching the first and second ends of the pair of force generating elements to respective first and second sets of teeth in each half-arch, the rigid framework in each half-arch including a pair of conjunction elements and a transverse element, each pair of conjunction elements configured to connect the ends of the telescoping members to one of the sets of teeth and the transverse element configured to interconnect the conjunction elements adjacent the ends of the telescoping members, the transverse element of at least one of the rigid frameworks forming at least one of the spring stops, wherein the pair of force generating elements is configured to generate forces between the first and second sets of teeth in a direction substantially perpendicular to the longitudinal axis of the arch to thereby move teeth of at least one of the first and second sets of teeth in a bodily manner.

2. The device of claim 1, wherein the telescoping elongated members of each force generating element comprise a tubular element and a rod-like element slidable within the tube-shaped element.

3. The device of claim 2, wherein the spring of each force generating element is a helix-shaped spring that is slidable on the tubular element.

4. The device of claim 2, wherein the spring of each force generating element is a helix-shaped spring that is slidable on the rod-like element.

5. The device of claim 1, wherein the at least one of the adjustable stops comprises a small buckle that is slidable on one of the elongated members, and a set screw which can be used to lock the buckle in place on the member.

6. The device of claim 5, wherein the small buckle is slidable on the tubular element.

7. The device of claim 1, wherein one of the pairs of conjunction elements is configured for attachment to at least one molar in the first set of teeth and the other of the pairs of conjunction elements is configured for attachment to at least one molar in the second set of teeth.

8. The device of claim 7, wherein the conjunction elements are elastically attached to strips configured to surround the at least one molar of each set.

9. The device of claim 7, wherein the conjunction elements are configured for rigid attachment to the at least one molar of each set by a soldered connection.

10. The device of claim 7, wherein each of the force generating elements generates a thrust force which pushes the at least one molar in the first and second sets away from each other.

11. The device of claim 10, wherein the rigid framework in each half-arch further includes an elongated member configured to interconnect the pair of conjunction elements adjacent the teeth and extend along and abut the lingual sides of teeth to thereby define the respective first and second sets, and wherein the thrust forces are transferred through the elongated members such that all the teeth in the first set are pushed away from all the teeth in the second set.

12. The device of claim 10, wherein one of the pairs of conjunction elements is configured for rigid attachment to two teeth in the first set and the other of the pairs of conjunction elements is configured for rigid attachment to two teeth in the second set, and wherein the thrust force is sufficient to expand the dental arch.

13. The device of claim 10, wherein each pair of the conjunction elements is configured such that one of the force generating elements is aligned with anterior incisors.

14. The device of claim 7, wherein the conjunction elements are configured such that the telescoping elongated members are located substantially between the at least one molar of the first and second sets.

15. The device of claim 7, wherein the conjunction elements are configured for attachment to the at least one molar of each set as close to the cervical zone as possible.

16. The device of claim 1, wherein one of the transverse elements forms a non-adjustable stop for one of the springs and the other of the transverse elements forms a non-adjustable stop for the other of the springs.

17. A device for orthodontic or orthopedic correction in a dental arch, the device comprising:

at least one force generating element having first and second ends and including a pair of telescopically engaged elongated members, a pair of stops, and a spring coaxial with the members and positioned intermediate the stops, wherein at least one of the stops is adjustable along an axial direction of the elongated members to regulate an amount of spring compression; and means for attaching the first and second ends of the at least one force generating element to respective first and second sets of teeth in the arch, one set of teeth being located in one half-arch and the other set of teeth being located in the other half-arch, each set of teeth including at least one tooth;

wherein the force generating element is configured to generate forces along the axis of the elongated telescoping members which are thereby transferred to the first and second sets of teeth in a direction substantially perpendicular to a longitudinal axis of the arch, the force generating element including a third elongated member fixedly attached to one of the pair of elongated members and slidably attached to the other of the pair of elongated members, the slidable attachment forming one of the pair of stops for the spring; and wherein the spring of the at least one force generating element is a compression spring configured to push against the slidable attachment formed by the third elongated member to generate a traction force which pulls the at least one tooth in the first set toward the at least one tooth in the second set.

18. The device of claim 17, wherein the elongated elements comprise a tubular element and a rod-like element slidable within the tubular element, and wherein the third elongated member is a wire having a first end secured to one of the rod-like element and the tubular element and a second end slidably attached to the other of the rod-like element and the tubular element, and which slidable attachment forms one of the pair of stops for the spring.

19. A device for orthodontic or orthopedic correction in a dental arch, the device comprising:

at least one force generating element having first and second ends and including a pair of telescopically engaged elongated members, a pair of stops, and a spring coaxial with the members and positioned intermediate the stops, wherein at least one of the stops is adjustable along an axial direction of the elongated members to regulate an amount of spring compression; and means for pitting first and second distinct sets of teeth against each other by attaching the first and second ends of the at least one force generating element to the respective first and second distinct sets of teeth in the arch with the at least one force generating element located on a buccal side of the teeth, both sets of teeth including at least one tooth in the half-arch, the attaching means configured to be fully supported by the first and second sets of teeth;

wherein the force generating element is configured to generate forces along the axis of the elongated telescoping members which are thereby transferred to the first and second sets of teeth in a direction substantially parallel to a longitudinal axis of the arch, and wherein the forces are exerted at a level of the basal gingiva to thereby move teeth of at least one of the first and second sets of teeth in a bodily manner.

20. The device of claim 19, wherein the first end of the at least one force generating element is configured for attachment to the at least one tooth in the first set of teeth as close to the cervical zone as possible, and wherein the second end of the at least one force generating element is configured for attachment to the at least one tooth in the second set of teeth as close to the cervical zone as possible.

21. The device of claim 19, wherein the at least one force generating element comprises a pair of force generating elements with one positioned in each half-arch and extending closely along the lingual sides of teeth therein.

22. The device of claim 21, wherein the at least one force generating element generates a thrust force which pushes at least one molar in each half-arch away from at least one anterior incisor.

23. The device of claim 22, wherein the pair of force generating elements include conjunction elements which overlap each other along the lingual faces of the at least one anterior incisor, and wherein the overlapping portions of the conjunction elements are fixedly secured together and configured to abut the at least one anterior incisor at a position as close to the cervical zone as possible.

24. A device for orthodontic or orthopedic correction in a dental arch, the device comprising:

at least one force generating element having first and second ends and including a pair of telescopically engaged elongated members, a pair of stops, and a spring coaxial with the members and positioned intermediate the stops, wherein at least one of the stops is adjustable along an axial direction of the elongated members to regulate an amount of spring compression; and means for attaching the first and second ends of the at least one force generating element to respective first and second distinct sets of teeth in the arch, both sets of teeth including at least one tooth in the half-arch;

wherein the force generating element is configured to generate forces along the axis of the elongated telescoping members which are thereby transferred to the first and second sets of teeth in a direction substantially parallel to a longitudinal axis of the arch and at a level of the basal gingiva, the force generating element including a third elongated member fixedly attached to one of the pair of elongated members and slidably attached to the other of the pair of elongated members, the slidable attachment forming one of the pair of stops for the spring; and wherein the spring of the at least one force generating element is a compression spring configured to push against the slidable attachment formed by the third elongated member to generate a traction force which pulls the teeth in the first and second sets towards each other.

* * * * *